US005837548A

United States Patent [19]
Weller et al.

[11] Patent Number: 5,837,548
[45] Date of Patent: Nov. 17, 1998

[54] TREATMENT OF INFLAMMATION BY INHIBITION OF LIPID BODY FORMATION

[75] Inventors: Peter F. Weller, Wellesley; Ann M. Dvorak, Newton; Patricia T. Bozza, Boston, all of Mass.

[73] Assignee: Beth Israel Hospital, Boston, Mass.

[21] Appl. No.: 565,869

[22] Filed: Dec. 1, 1995

[51] Int. Cl.$^6$ .................................................. G01N 33/48
[52] U.S. Cl. .............................................. 436/63; 514/886
[58] Field of Search ................................ 436/63; 514/888

[56] References Cited

U.S. PATENT DOCUMENTS

| | | | |
|---|---|---|---|
| 5,409,710 | 4/1995 | Leonard | 424/489 |
| 5,449,679 | 9/1995 | Leonard | 514/310 |

FOREIGN PATENT DOCUMENTS

| | | |
|---|---|---|
| 289667 | 11/1988 | European Pat. Off. . |
| WO94/08038 | 4/1994 | WIPO . |

OTHER PUBLICATIONS

Vane, J., "Toward a better aspirin," *Nature* 367: 215–216 (1994).

Langenbach, R., et al., "Prostaglandin Synthase 1 Gene Disruption in Mice Reduces A rachidonic Acid–Inducing Inflammation and Indomethacin–Induced Gastric Ulceration," *Cell*, 483–492 (1995).

Morham, S. G., et al., "Prostaglandin Synthase 2 Gene Disruption Causes Severe Renal Pathology in the Mouse," *Cell* 83: 473–482 (1995).

Weller, P. F. et al., "Cytoplasmic Lipid Bodies of Human Eosinophils," *Am. J. of Pathology*, 138(1) : 131–148 (1991).

Dvorak, A.M., et al., "Ultrastructural Immunogold Localization of Prostaglandin Endoperoxide Synthase (Cylooxygenase) to Non–membrand–bound Cytoplasmic Lipid Bodies in Human Lung Mast Cells, Alveolar Macrophages, Type II Pneumocytes, and Neutrophils," *The J. of Histochemistry and Cytochemistry*, 40(6) : 759–769 (1992).

Dvorak, A. M., et al., "Prostaglandin Endoperoxide Synthase (Cyclooxygenase) : Ultrastructural Localization to Nonmembrane–Bound Cytoplasmic Lipid Bodies in Human Eosinophils and 3T3 Fibroblasts," *Int Arch Allergy Immunol,* 105: 245–250 (1994).

Dvorak, A. M., et al., "Human Lung Mast Cell and Alveolar Macrophage Cytoplasmic Lipid Bodies contain Arachidonic Acid and Prostaglandin Endoperoxide Synthase (Cyclooxygenase), the Substrate and Enzyme Necessary for Prostaglandin Production," *Int Arch Allergy Immunol,* 99: 208–217 (1992).

Dvorak, A. M. et al., "Ultrastructural Localization of Prostaglandin Endoperoxide Synthase (Cyclooxygenase) to Isolated, Purified Fractions of Guinea Pig Peritoneal Macrophage and Line 10 Hepatocarcinoma Cell Lipid Bodies," *Int Arch Allergy Immunol,* 191: 136–142 (1993).

Beil, W. J., et al., "Ultrastructural immunogold localization of subcellular sites of TNF–α in colonic Crohn'disease," *J. of Leukocyte Biology,* 58: 284–298 (1995).

Weller, P. F., and Dvorak, A. M., "Lipid bodies: Intracellular site for eicosanoid formation," *J. Allergy Clin Immunol.,* 94(64) (Part 2): 1151–1156 (1994).

Vane, J.R., "Inhibition of Prostaglandin Synthesis as a Mechanism of Action for Aspirin–Like Drugs", *Nature 231*: 232–235 (1971).

Weller, R.F., et al., "Cytoplasmic Lipid Bodies of Human Neutrophilic Leukocytes", *Am. J. Pathology,* 135(5): 947–959 (1989).

Weller, P.F., and Dvorak, A.M., "Arachidonic Acid Incorporation by Cytoplasmic Lipid Bodies of Human Eosinophils", *Blood,* 65(5): 1269–1274 (1985).

Dvorak, A.M., et al., "Lipid Bodies: Cytoplasmic Organelles Important to Arachidonate Metabolism in Macrophages and Mast Cells," *J. Immunology,* 131(6): 2965–2976 (1983).

Weller, P. F., et al., "Cytoplasmic Lipid Bodies of Neutrophils: Formation Induced by cis–Unsaturated Fatty Acids and Mediated by Protein Kinase C," *J. Cell Biol.,* 113(1): 137–146 (1991).

Sigal, E., "The Molecular Biology of Mammalian Arachidonic Acid Metabolism," *Am J. Physiol,* 260: L13–L28 (1991).

Laposata, M., et al., "Icosanoid Production Can Be Decreased without Alterations in Cellular Arachidonate Content or Enzyme Activities Required for Arachidonate Release and Isosanoid Synthesis," *J. Biol. Chem,* 263(7): 3266–3273 (1988).

Giovannucci, E., et al., "Aspirin Use and the Risk for Colorectal Cancer and Adenoma in Male Health Professional", *Annals Intern Medicine,* 121(4): 241–246 (1994).

Thun, M. J., et al., "Asprin Use and Risk of Fatal Cancer," *Cancer Res.,* 53: 1322–1327 (1993).

Greenberg, E. R., et al., "Reduced Risk of Large–Bowel Adenomas Among Asprin Users," *J. Nat. Cancer Inst,* 85(11): 912–916 (1993).

(List continued on next page.)

Primary Examiner—C. Warren Ivy
Assistant Examiner—Charanjit S. Aulakh
Attorney, Agent, or Firm—Hamilton, Brook, Smith & Reynolds, P.C.

[57] ABSTRACT

The present invention provides a method for treating a lipid body-mediated condition, such as inflammation or cancer, in an vertebrate by administering to the vertebrate a sufficient amount of an agent which inhibits the formation of lipid bodies in cells involved in inflammation. The agent can inhibit lipid body formation by inhibiting any biological activity necessary for lipid body formation.

Another embodiment of the present invention is a method or assay for assessing the ability of a compound to inhibit lipid body formation in cells in vitro. The method comprises the steps of priming the cells for lipid body formation, contacting the cells with the compound under study, and comparing lipid body numbers in the cells with lipid body numbers in primed cells not contacted with the compound of interest. This method can be automated, yielding an efficient high-throughput assay for the efficient and rapid screening of large numbers of potential anti-inflammatory drugs.

22 Claims, 5 Drawing Sheets

OTHER PUBLICATIONS

Nissen, H, M., "On Lipid Droplets in Renal Interstitial Cells, II. A Histological Study on the Number of Droplets in Salt Depletion and Acute Salt Repletion", *Zeitschrift für Zellforsehung* 85:483–491 (1968).

Bozza, P. T. et al., "Mechanisms of Platelet–activating Factor–inducing Lipid Body Formation: Requisite Roles for 5–Lipoxygenase and De Novo Protein Synthesis in the Compartmentalization of Neutrophil Lipids", *J. Exp. Med, The Rockefeller University Press, vol. 183*: 1515–1525 (Apr. 1996).

Hexeberg, S. et al., "Docosahexaenoic acid induces lipid accumulation in myocardial cells of rats", *Scand J. Clin Lab Invest,* 54: 665–671 (1994).

Weller, P. F. et al., "Cytoplasmic Lipid Bodies of Human Neutrophilic Leukocytes", *Am. J. of Pathology 135*(5): 947–959 (Nov. 1989).

Weller, P. F. et al., "Cytoplasmic Lipid Bodies of Human Eosinophils", *Am. J. of Pathology, 138*(1): 141–148 (Jan. 1991).

TREATMENT OF INFLAMMATION BY INHIBITION OF LIPID BODY FORMATION

FUNDING STATEMENT

The invention described herein was supported in whole or in part by Grant No. AI 20257 from the National Institutes of Health. The United States Government has certain rights in the invention.

BACKGROUND OF THE INVENTION

The inflammatory response is elicited by numerous different stimuli, such as infectious agents, ischemia, antigen-antibody interactions, and thermal and other physical injury (Insel, in *The Pharmacological Basis of Therapeutics* Eighth Edition, Gilman et al., eds., Pergamon Press, New York, 638–653 (1990)). Symptoms of inflammation include erythema, edema, tenderness and pain and are most commonly managed by the administration of nonsteroidal anti-inflammatory drugs (NSAIDs), such as aspirin and ibuprofen. The activity of these agents has been attributed to their ability to inhibit cyclooxygenase, the key rate-determining enzyme in the prostaglandin biosynthetic pathway (Vane, *Nature New Biol.* 231:232 (1971); Ferreira et al., *Ann. Rev. Pharmacol.* 14:57 (1974)).

The NSAIDs have common side effects which limit their usefulness in certain situations (Insel (1990), supra). Among the most prominent is gastric or intestinal ulceration, often accompanied by anemia from resultant blood loss. Other side effects include disturbances in platelet function and prolongation of gestation. In patients suffering from congestive heart failure, hepatic cirrhosis or chronic renal disease, acute renal failure may result. Moreover, aspirin cannot be administered to children because of its association with Reye's syndrome. These side effects, in general, are due to inhibition by these drugs of prostaglandin-mediated processes other than inflammation. Gastrointestinal ulceration, for example, results from the inhibition of gastric prostaglandins which suppress acid secretion in the stomach and stimulate intestinal mucus secretion.

The need for new anti-inflammatory drugs which overcome the disadvantages associated with those in current use continues. Inflammation is a complex process with presumably many potential points for drug intervention waiting to be found. The discovery of novel anti-inflammatory drugs also depends upon the development of new methods for screening drug candidates. Traditional methods for screening compounds for anti-inflammatory activity involve a battery of tests, each assessing a particular biological activity, such as cyclooxygenase inhibition. Alternately, or in addition, the activity of a potential anti-inflammatory drug is evaluated in an animal model of inflammation. Each of these methods for evaluating potential anti-inflammatory drugs is time-consuming and costly. Thus, the need exists for an efficient method for rapidly screening large numbers of compounds for anti-inflammatory activity.

SUMMARY OF THE INVENTION

The present invention relates to treatment of conditions in individuals which result from lipid body formation or function, referred to as "lipid body-mediated conditions", such as treatment of inflammation and cancer/malignancies (e.g., carcinomas, sarcomas, lymphomas, and leukemias).

In one embodiment, the present invention is based on the role of lipid bodies in inflammation. As described herein, Applicants have demonstrated that lipid bodies serve as sites for eicosanoid biosynthesis in cells involved in inflammation. The invention is a method for treating inflammation in a vertebrate, for example, a human, by administering to the vertebrate in sufficient amount an agent which inhibits, partially or completely, the formation of lipid bodies in cells involved in inflammation. As used herein, the term "treating inflammation" includes preventing, reducing, or reversing inflammation in an individual. The agent can inhibit lipid body formation by suppressing any process necessary for lipid body formation, including fatty acid uptake, protein synthesis and intracellular signaling, involving, for example, protein kinase C and phospholipase C. Cells which can be targets for these agents include leukocytes, such as neutrophils, eosinophils, lymphocytes, monocytes and macrophages, in addition to endothelial cells, epithelial cells, platelets, mesenchymal cells, including fibroblasts, and tumor cells.

In a further embodiment, the present invention relates to treating (preventing, reducing or reversing) cancers through the use of agents which inhibit lipid body formation and/or function in the cancerous cells. The agents effective for treating cancer by inhibiting lipid body formation and/or function can do so by suppressing any process, such as those described in the previous paragraph, necessary for their formation or function.

Another embodiment of the present invention is a method or assay for assessing the ability of a compound to inhibit lipid body formation. In one embodiment of the method, the ability of a compound (referred to as "compound of interest") to inhibit lipid body formation is assessed in cells, for example, human leukocytes, primed for lipid body formation. The cells may be primed for lipid body formation prior to, simultaneous with, or subsequent to being contacted with the compound of interest. The extent to which lipid bodies are formed in the presence of the compound of interest is compared with the extent to which they are formed in the absence of the compound of interest. The compound of interest can be assessed by this method at varying concentrations in order to determine, for example, the minimum quantity of the agent sufficient to inhibit lipid body formation and thus, treat inflammation or the optimum quantity for doing so. In one embodiment, the method comprises the steps of: (1) contacting cells with the compound of interest under conditions appropriate for lipid body formation; (2) priming the cells for lipid body formation; (3) determining the extent of lipid body formation in the cells; and (4) comparing the extent of lipid body formation in the cells to the extent of lipid body formation in control cells, which are primed as in step (2) but not contacted with the compound of step (1).

The control of step (4), above, can be carried out previous to, simultaneously with, or subsequent to assessment of the compound of interest. In one embodiment, the results determined with the compound of interest are compared with a pre-determined standard or reference (i.e., the control is established prior to testing of a compound of interest). Steps (1) and (2) above need not be carried out in the indicated order. Priming of cells for lipid body formation may precede contacting the cells with the compound of interest, or both steps may be conducted simultaneously. Formation of fewer lipid bodies in cells contacted with the compound of interest than in the control cells indicates the ability of the compound of interest to inhibit lipid body formation (i.e., that the compound of interest is an inhibitor of lipid body formation). Cells which can be used in this method include leukocytes, platelets, muscle cells, mesenchymal cells, including fibroblasts, endothelial cells, epithelial cells, tumor cells and cell lines derived from any of these cell types.

A particular advantage of the present method or assay is the ability to detect compounds interfering with lipid body formation and, thus, the inflammatory response, at many different points. This method can, therefore, identify potential anti-inflammatory agents that would go unrecognized by standard screening methods, such as the assessment of ability to inhibit cyclooxygenase. An additional advantage of this method is that it can be automated to provide a high-throughput assay capable of rapidly screening large numbers of compounds for anti-inflammatory activity.

DETAILED DESCRIPTION OF THE INVENTION

Figure 1A:
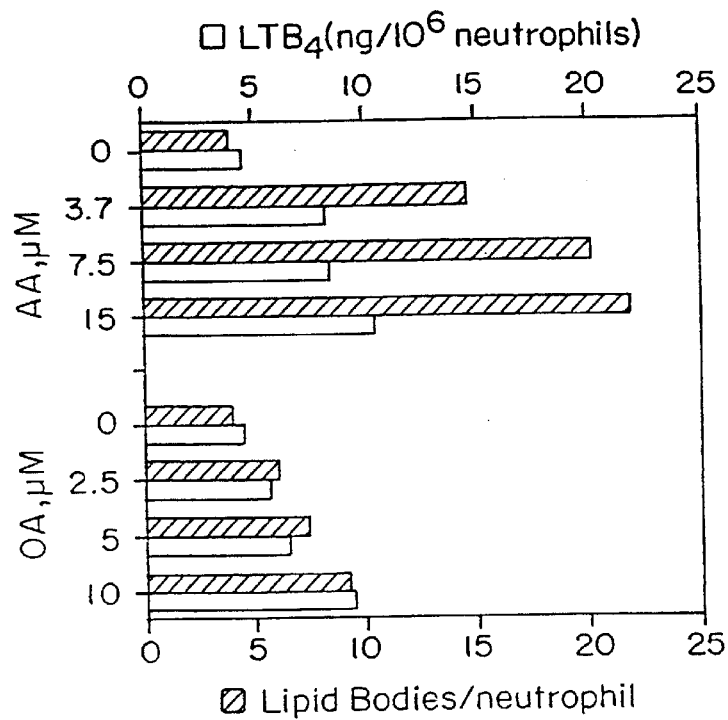
FIG. 1A is a graph illustrating the effect of arachidonic acid (AA) and oleic acid (OA) on induction of lipid body formation (black) and priming effects (white) for enhanced leukotriene B4 ($LTB_4$) by human neutrophils. Neutrophils ($10^6$/mL) were stimulated for one hour with arachidonic acid (3.7, 7.5, 15 $\mu$M) or oleic acid (2.5, 5, 10 $\mu$M). Lipid bodies were enumerated using light microscopy following osmium staining. The concentration of $LTB_4$ in the supernatant was measured by ELISA after incubation with A23187 (0.5 $\mu$M) for 15 minutes at 37° C. Data are expressed as mean from 2–3 independent assays performed in duplicate.
Figure 1B:
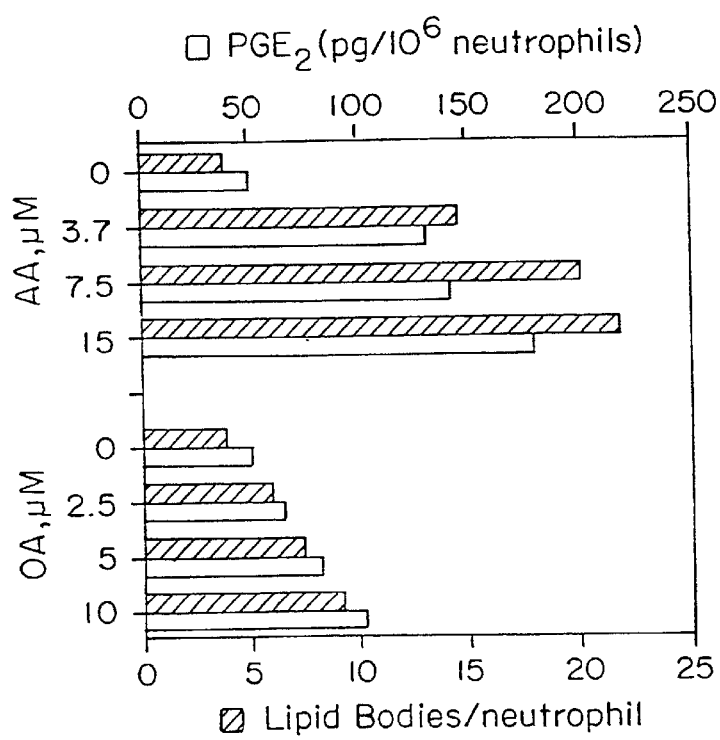
FIG. 1B is a graph showing the effect of arachidonic acid (AA) and oleic acid (OA) on lipid body induction (black) and priming for enhanced prostaglandin $E_2$ ($PGE_2$) production (white) by human neutrophils. Neutrophils ($10^6$/mL) were stimulated for one hour with arachidonic acid (3.7, 7.5, 15 $\mu$M) or oleic acid (2.5, 5, 10 $\mu$M). Lipid bodies were enumerated using light microscopy following osmium staining. The concentration of $PGE_2$ in the supernatant was measured by ELISA after incubation with A23187 (0.5 $\mu$M) for 15 minutes at 37° C. Data are expressed as mean from 2–3 independent assays performed in duplicate.
Figure 2A:
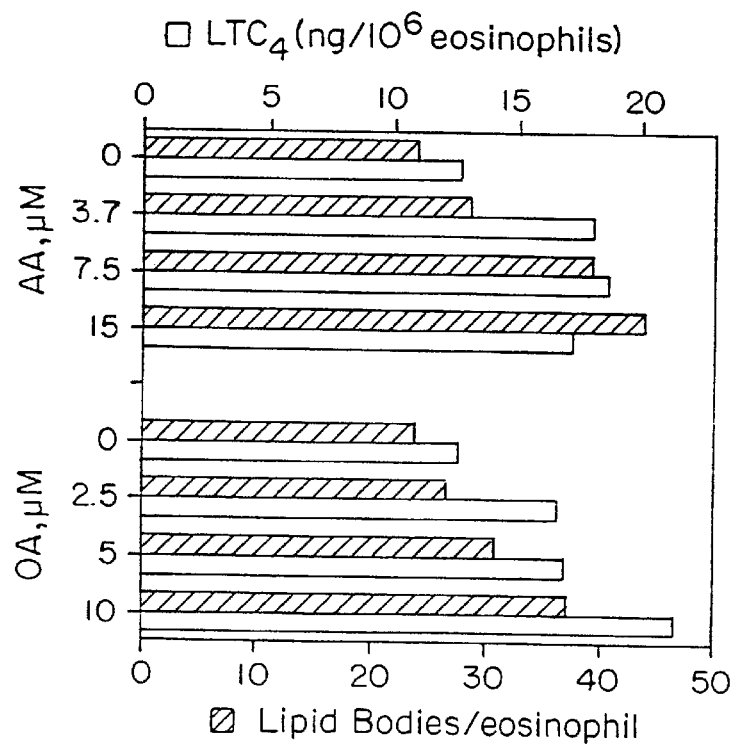
FIG. 2A is a graph illustrating the effect of arachidonic acid (AA) and oleic acid (OA) on induction of lipid body formation (black) and priming effects (white) for enhanced leukotriene $C_4$ ($LTC_4$) by human eosinophils. Eosinophils ($10^6$/mL) were stimulated for one hour with arachidonic acid (3.7, 7.5, 15 $\mu$M) or oleic acid (2.5, 5, 10 $\mu$M). Lipid bodies were enumerated using light microscopy following osmium staining. The concentration of $LTC_4$ in the supernatant was measured by ELISA after incubation with A23187 (0.5 $\mu$M) for 15 minutes at 37° C. Data are expressed as mean from 2 independent assays performed in duplicate.
Figure 2B:
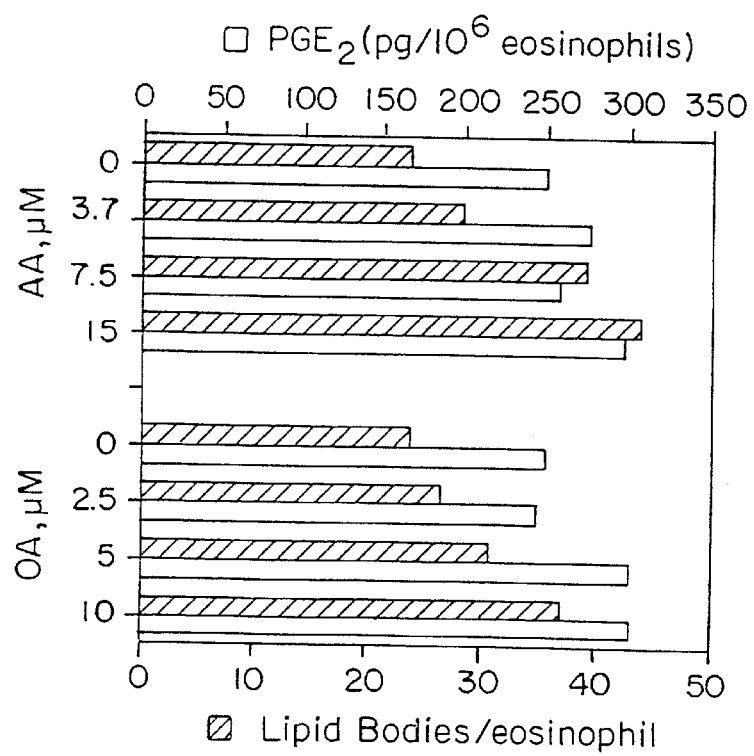
FIG. 2B is a graph illustrating the effect of arachidonic acid (AA) and oleic acid (OA) on induction of lipid body formation (black) and priming effects (white) for enhanced prostaglandin $E_2$ ($PGE_2$) by human eosinophils. Eosinophils ($10^6$/mL) were stimulated for one hour with arachidonic acid (3.7, 7.5, 15 $\mu$M) or oleic acid (2.5, 5, 10 $\mu$M). Lipid bodies were enumerated using light microscopy following osmium staining. The concentration of $PGE_2$ in the supernatant was measured by ELISA after incubation with A23187 (0.5 $\mu$M) for 15 minutes at 37° C. Data are expressed as mean from 2 independent assays performed in duplicate.

The present invention relates to a method for treating inflammation in a vertebrate, including mammals, such as humans, mice, rats, guinea pigs, dogs, cats, horses and pigs, by administering to the vertebrate an agent which inhibits lipid body formation. The agent can inhibit lipid body formation by suppressing any process necessary for lipid body formation, including fatty acid release or uptake, receptor-mediated stimulation, gene activation and transcription, protein synthesis and intracellular signaling, involving, for example, protein kinase C and phospholipase C. The invention further provides a method or assay for screening a potential anti-inflammatory agent by assessing the ability of the agent to inhibit lipid body formation in cells primed for lipid body formation in vitro.

Lipid bodies are lipid-rich organelles found in a diversity of cell types, including leukocytes, mast cells, endothelial cells, epithelial cells and fibroblasts (Galli et al. in Bailey, ed., *Prostaglandins, Leukotrienes and Lipoxins*, Plenum, New York, 221–239 (1985); Weller et al. *Am. J. Path.* 135:947–959; Weller et al., *Blood* 65:1269–1274 (1985); Dvorak et al. *J. Immunol.* 131:2965–2976 (1983)). These distinct cytoplasmic structures are approximately spherical with diameters generally ranging from 0.2 to 2 μm, and contain protein in addition to lipid. Although typically scarce in normal cells, lipid bodies increase in number and size in cells associated with inflammation. For example, neutrophils from healthy human subjects contain, on average, fewer than 0.7 lipid bodies per cell, while peripheral blood neutrophils isolated from patients with bacterial infections contain many more lipid bodies each (Weller et al., *J. Cell Biol.* 113:137–146 (1991)). Additional observations of increased numbers of lipid bodies in human neutrophils associated with various inflammatory responses demonstrate that lipid body formation is a natural process that correlates with participation by cells in inflammation (Weller et al., *J. Allergy Clin. Immunol.* 94:1151–1156 (1994)).

A role for lipid bodies in the inflammatory response has recently been elucidated. Lipid bodies serve as storage sites for cell-incorporated arachidonate, the precursor of the eicosanoid mediators of inflammation which include prostaglandins, leukotrienes and thromboxanes (Weller et al., *Am. J. Pathol.* 138:141–148 (1991)). Recent work has identified among the protein components of lipid bodies enzymes necessary for eicosanoid production, such as lipoxygenases, cyclooxygenase (prostaglandin endoperoxide synthase), lipases and protein kinase C (Dvorak et al., *J. Histochem. Cytochem.* 40:759–769 (1992); Dvorak et al., *Int. Arch. Allergy Immunol.* 101:136–142 (1993); Dvorak et al. *Int. Arch. Allergy Immunol.* 105:245–250 (1994)). Thus, lipid bodies contain all of the components necessary to serve as sites of eicosanoid biosynthesis.

It is generally believed that eicosanoid biosynthesis occurs only at cell membranes (Sigal, *Am. J. Physiol.* 260:L13–L28 (1991)). However, additional experimental evidence supports a role for lipid bodies as sites of eicosanoid biosynthesis. For example, cells producing prostaglandin $E_2$ lost the ability to release this compound when deprived of exogenous arachidonate for a period of 24 to 48 hours. However, levels of total membrane arachidonate and relevant enzymes remained normal during this period, prompting the suggestion that arachidonate was depleted from an unspecified intracellular pool (Laposata et al., *J. Biol. Chem.* 263:3266–3273 (1988)). Utilizing lipid bodies as the source for eicosanoid precursors avoids the membrane perturbation expected upon removal of a significant amount of arachidonate from the membrane. The converse has been established in lymphocytes, which form lipid bodies to avoid membrane perturbation in response to exogenous fatty acids (Stubbs et al., Biochemistry 19:2756–2762 (1980)). In one model, the relatively small quantities of arachidonate needed for formation of autocrine eicosanoids or for second messenger activities are derived from the cell membrane, while the larger amounts of arachidonate needed for eicosanoids used as paracrine mediators, as in inflammation, come from lipid body stores.

Lipid bodies form rapidly as the product of a complex signaling pathway. Incubation of human neutrophils with cis-unsaturated fatty acids induces lipid body formation in a dose-dependent fashion, while saturated fatty acids elicit no response (Weller et al., *J. Cell Biol.* 113:137–146 (1991)). This may be due to the ability of cis-unsaturated fatty acids to activate protein kinase C, which is not shared by saturated fatty acids. Other activators of protein kinase C, including 1-oleyl-2-acetyl-rac-glycerol and phorbol-12-myristate-13-acetate, also induce lipid body formation. In each case, induced lipid body formation was suppressed by inhibitors of protein kinase C or phospholipase C. Lipid body formation is also induced by platelet activating factor via a receptor-mediated process requiring lipoxygenase activity but not cyclooxygenase activity. Finally, formation of lipid bodies requires de novo protein synthesis and is, therefore, inhibited by inhibitors of mRNA synthesis and ribosomal activity.

For the purposes of the present invention, "inhibition" of lipid body formation is intended to include the inhibition of an increase in lipid body number and/or lipid body size in a cell; inhibition may be partial or complete.

"Contacting" is intended to include methods of bringing the compound to be tested for activity in inhibiting lipid body formation into direct contact with the cells which form lipid bodies.

"Priming" of cells for lipid body formation is intended to comprise all means of inducing cells to form lipid bodies, and includes contacting cells with an agent which induces lipid body formation.

The term "cis-unsaturated fatty acid" is intended to include fatty acids with one or more carbon-carbon double bonds, in which the substituents on the $sp^2$-hybridized carbon atoms display cis stereochemistry.

As Applicants describe herein, they have shown that certain anti-inflammatory agents, including aspirin and other NSAIDs, inhibit the cis-unsaturated fatty acid-induced formation of lipid bodies in activated human neutrophils and eosinophils. The function of lipid bodies as sites of eicosanoid biosynthesis in cells involved in inflammation indicates that the ability of the NSAIDs to inhibit lipid body formation contributes significantly to the anti-inflammatory activity of these drugs, independent of the well-recognized activity of several of these as inhibitors of cyclooxygenase.

As a first step in the elucidation of the mechanism of cis-unsaturated fatty acid-induced lipid body formation, the dependence of this process on protein kinase C (PKC) signaling was investigated. The PKC inhibitors staurosporine and chelerythrine significantly inhibited cis-unsaturated fatty acid-induced lipid body formation. Second, two specific inhibitors of phospholipase C (PLC) were also shown to reduce lipid body formation induced by cis-unsaturated fatty acids. In addition, inhibitors of gene transcription and protein synthesis also suppressed lipid body formation in the presence of cis-unsaturated fatty acids. Thus, fatty acid-induced lipid body formation is dependent upon signaling pathways involving PKC and PLC as well as de novo protein synthesis. Treatment of human neutrophils and eosinophils with either arachidonic acid or oleic acid resulted in a dose-dependent increase in the number of lipid bodies present, as well as a dose-dependent increase in production of prostaglandin $E_2$ ($PGE_2$) and leukotriene $B_4$ ($LTB_4$) by neutrophils and leukotriene $C_4$ ($LTC_4$) by eosinophils. Thus, an increase in lipid body numbers correlates with increased eicosanoid production.

The effects of aspirin and other NSAIDs on cis-unsaturated fatty acid-induced lipid body formation were also investigated. Aspirin, indomethacin and piroxicam, which are cyclooxygenase inhibitors, and sodium salicylate, which is not a cyclooxygenase inhibitor, all caused significant inhibition of cis-unsaturated fatty acid-induced lipid body formation. Additional evidence showed that this was not due to inhibition of fatty acid uptake by the cell. This effect was further shown to be independent of cyclooxygenase activity by comparing wild-type murine peritoneal macrophages with macrophages from cyclooxygenase-1 and cyclooxygenase-2 knockout mice. No differences in lipid body formation were evident between normal and cyclooxygenase deficient cells and both indomethacin and sodium salicylate significantly inhibited cis-unsaturated fatty acid-induced lipid body formation in both sets of cells.

The ability of aspirin to inhibit the production of lipoxygenase-derived eicosanoids was also shown. Aspirin inhibited cis-unsaturated fatty acid priming for $LTB_4$ formation in human neutrophils and $LTC_4$ formation in human eosinophils. Aspirin, however, is not a direct inhibitor of lipoxygenase, and, thus, must interfere with leukotriene biosynthesis upstream of the lipoxygenase-catalyzed oxidation of arachidonate, apparently by inhibiting lipid body formation.

The foregoing results indicate that aspirin and the other NSAIDs investigated inhibit the inflammatory response by a method or methods other than cyclooxygenase inhibition. This is unexpected because the anti-inflammatory activity of most NSAIDs, including aspirin, has previously been attributed solely to their ability to inhibit prostaglandin biosynthesis via inhibition of cyclooxygenase (Vane, *Nature* 367:215–216 (1994); Vane (1971), supra; Ferreira et al. (1974), supra). These results, however, demonstrate that suppression of lipid body formation is useful for inhibiting inflammation.

Recent evidence demonstrates a role for NSAIDs in the prevention of certain cancers. Humans who take aspirin or other NSAIDs regularly have a 40–50% lower risk of developing colorectal cancer compared to persons not taking these drugs. (Giovannucci et al., *Ann. Intern. Med.* 121: 241–246 (1994); Greenberg et al., *J. Nat. Cancer Inst.* 85:912–916 (1993); Thun et al., *Cancer Res.* 53:1322–1327 (1993)). This result, and the observation of enhanced lipid body formation in a variety of carcinoma, sarcoma, and lymphoma cells (Galli et al. (1985), supra), supports the conclusion that this protective effect of NSAIDs is due to their ability to inhibit lipid body formation. Thus, administering to a vertebrate, such as a human, an agent which inhibits lipid body formation is useful for the prevention or treatment of many cancers.

The present method for treating lipid body-mediated conditions, such as inflammation and cancers, in a vertebrate, for example, a human, comprises administering to the vertebrate, in sufficient amount, an agent which inhibits, partially or completely, the formation of lipid bodies in the cytoplasm or nucleus of cells involved in inflammation or in cancerous cells. Such cells include leukocytes, such as neutrophils, eosinophils, lymphocytes, monocytes, and macrophages, as well as platelets, vascular endothelial cells, epithelial cells, mesenchymal cells, including fibroblasts, and varied neoplastic or tumor cells. The agent can inhibit lipid body formation by suppressing any process necessary for lipid body formation, including fatty acid uptake, receptor-mediated stimulation, gene activation, gene transcription, protein synthesis and intracellular signaling, involving, for example, protein kinase C and phospholipase C.

The agents which inhibit lipid body formation, described above, can be used in the treatment of inflammation in a vertebrate by administering to the vertebrate, for example, a human, a therapeutically effective amount of the agent or combination of agents. The quantity of an individual agent to be administered will be determined on an individual basis and will be determined, at least in part, by consideration of the individual's size and gender, the severity of symptoms to be treated and the result sought. The agent may be administered alone or in a pharmaceutical composition comprising the agent and an acceptable carrier or diluent.

The agents can be administered by a parenteral or a non-parenteral route, including, but not limited to, subcutaneous or other injection, intravenously, topically, orally, transdermally, rectally or nasally. The form in which the agent will be administered, for example, powder, tablet, capsule, solution, or emulsion, will depend on the route by which it is administered. The therapeutically effective amount can be administered in a single dose or in a series of doses separated by appropriate time intervals, such as hours.

Another embodiment of the present invention is a method or assay for assessing the ability of a compound, at varying concentrations, to inhibit lipid body formation in cells. In one embodiment of the method, which is carried out in vitro, the ability of a compound to inhibit lipid body formation is assessed in cells, for example, human leukocytes, which are primed for lipid body formation. The extent to which lipid bodies are formed in the presence of the compound of interest is compared with the extent to which they are formed in the absence of the compound of interest. This embodiment comprises the steps of: (1) contacting the cells with the compound of interest under conditions appropriate for lipid body formation; (2) priming the cells for lipid body formation; (3) determining the extent of lipid body formation in the cells; and (4) comparing the extent of lipid body formation in the cells to the extent of lipid body formation in control cells, which are primed as in step (2) but not contacted with the compound of step (1). Steps (1) and (2) above need not be carried out in the indicated order. Priming of cells for lipid body formation can precede contacting the cells with the compound of interest, or both steps can be conducted simultaneously.

The control cells of step (4), above, can be established previous to, simultaneous with, or subsequent to assessment of the compound of interest. In one embodiment, the results determined with the compound of interest are compared with a pre-determined standard or reference (i.e., the control is established prior to testing of a compound of interest). Formation of fewer lipid bodies in cells contacted with the compound of interest than in the control cells indicates the ability of the compound of interest to inhibit lipid body formation (i.e., that the compound of interest is an inhibitor of lipid body formation).

Any human or animal cell which is involved in inflammation can be used in this method. Cells which can be used include, but are not limited to, leukocytes such as neutrophils, eosinophils, lymphocytes, monocytes, and macrophages, in addition to muscle cells, platelets, mesenchymal cells, fibroblasts, endothelial cells, tumor cells, and cell lines derived from these various cell types. The cells may be primed for lipid body formation by any means known to induce lipid body formation, including, but not limited to, contacting the cells with PKC activators, such as phorbol esters, diglycerides and cis-unsaturated fatty acids, and stimuli that lead to generation of these fatty acids. Cis-unsaturated fatty acids of use in the present method include arachidonic acid and oleic acid. Phorbol esters which can be used in the method include phorbol-12-myristate-13-acetate and phorbol-12,13-dibutyrate, while appropriate diglycerides include 1-oleoyl-2-acetyl-rac-glycerol. Other compounds which elicit lipid body formation in human neutrophils and eosinophils via receptor-mediated processes include 5-hydroxy-6,8,11,14-eicosatetraenoic acid (5-HETE), 12-HETE, 15-HETE and platelet-activating factor (PAF). In addition, lipid body formation may be induced by hypoxia.

In one embodiment of the present method, the extent of lipid body formation in cells may be determined by enumeration of the lipid bodies formed. This can be accomplished, for example, by staining lipid bodies within the cells, mounting the cells and visually counting the lipid bodies within cells. The components of lipid bodies are, in general, osmiophilic and can be selectively stained with an osmium compound such as osmium tetroxide. Lipid bodies may also be stained with a lipophilic fluorescent dye, such as Nile red, or by the incorporation of fluorescent lipids, such as fatty)acids. Visual counting can be performed with the aid of light or electron microscopy.

In yet another embodiment of the present invention, the method for determining the ability of a compound to inhibit lipid body formation is automated, providing a high throughput assay able to rapidly screen large numbers of compounds. Means known in the art can be utilized to automatically perform the steps of the method, including visualization and determination of the extent of lipid body formation.

An agent shown, in the in vitro method described above, to inhibit lipid body formation can be evaluated for in vivo efficacy in an appropriate animal model or in humans.

The present method overcomes the limitations of current assays for anti-inflammatory activity. A particular advantage of the present method is that it identifies compounds interfering with lipid body formation, and thus inflammation, at any point in this process. Thus, it is not restricted to compounds employing a specific mechanism of lipid body inhibition. A further advantage is the adaptability of the method to automation, thereby allowing efficient screening of large numbers of drug candidates via a high-throughput assay.

EXAMPLES

General Materials and Methods

The following procedures and materials were employed in Examples 1–3 below. Additional experimental details specific to a given example are provided with that example.

Aspirin, indomethacin, piroxicam, salicylic acid (sodium salt), oleic acid, arachidonic acid, and the protein synthesis inhibitors cycloheximide and actinomycin D were obtained from Sigma Chemical Co. (St. Louis, Mo.). Staurosporine, chelerythrine, and A23187 were from Calbiochem (La Jolla, Calif.). The phospholipase C (PLC) inhibitors D609 and U-73122 were from BIOMOL (Plymouth Meeting, Pa.).

Human Neutrophil and Eosinophil Purification

Neutrophils were purified from fresh human blood obtained by venipuncture from healthy adult volunteers and collected into acidified citrate. After addition of 6% dextran 70 (McGaw, Irvine, Calif.), RBCs were allowed to sediment for 1 hour at room temperature. The leukocyte-rich supernatant was overlaid onto an equal volume of Ficoll-Paque gradient (Piscataway, N.J.), and centrifuged at 400×g for 20 min. PMNs (>95% pure, rest being eosinophils) were recovered from the pellet and washed in $Ca^{++}/Mg^{++}$ free HBSS. Residual RBCs were lysed with hypotonic saline. Eosinophils (80% pure, the rest being neutrophils) were obtained from a donor with idiopathic hypereosinophilic syndrome using the same procedure as described above.

Lipid Body Induction and Treatment

Human leukocytes ($10^6$ cells/mL) were incubated with varying concentrations of arachidonic acid (AA), oleic acid (OA) or vehicle at 37° C. in a 5% $CO_2$/95% $O_2$ atmosphere, and after 1 hour leukocytes ($10^5$ cells per slide) were cytocentrifuged (550 rpm, 5 min) onto glass slides. During inhibitory studies, neutrophils were pretreated for 1 hour with varying concentrations of enzyme inhibitors, protein synthesis inhibitors, or vehicle as indicated. When PKC inhibitors were used, the pre-incubation time was reduced to 30 minutes to avoid toxic effects to the cells. The cell viability, determined by trypan blue dye exclusion at the end of each experiment, was always greater than 90%. Stock solutions for A23187, D609, U-73122, and indomethacin were prepared in DMSO and stored at −20° C. Aliquots were diluted in $Ca^{++}/Mg^{++}$ fee HBSS to the indicated concentration immediately prior to use. The final DMSO concentration was always lower than 0.1% and had no effect on lipid body numbers. Aspirin, piroxicam, sodium salicylate, staurosporine, chelerythrine, cycloheximide, and actinomycin D were diluted in $Ca^{++}/Mg^{++}$free HBSS, pH 7.4, rinsed in 0.1M cacodylate buffer pH 7.4, stained in 1.5% $OsO_4$ (30 min), rinsed in $dH_2O$, immersed in 1.0% thiocarbohydrazide (5 min), rinsed in 0.1M cacodylate buffer, restained in 1.5% $OsO_4$ (3 min), rinsed in $dH_2O$, and then dried and mounted. The morphology of fixed cells was observed, and lipid bodies were enumerated with phase contrast microscopy and a 100× objective lens in 50 consecutively scanned leukocytes.

Statistical Analysis

Results were expressed as mean±SEM and were analyzed statistically by means of the analysis of variance followed by the Newman-Keuls-Student test with the level of significance set at p<0.05. Correlation coefficients were determined by linear regression, and correlation analysis was performed by Fisher's r to z transformation with the level of significance set at p<0.05.

Example 1

Investigation of the Mechanism of cis-unsaturated Fatty Acid-Induced Lipid Body Formation Materials and Methods Purification of human leukocytes, treatment of leukocytes with enzyme inhibitors and enumeration of lipid bodies were performed as described above.

Results

This study revealed that cis-unsaturated fatty acid-induced lipid body formation is dependent upon protein kinase C, phospholipase C and de novo protein synthesis. Previous work had shown that arachidonic acid and oleic acid elicited dose-dependent increases in lipid body formation in both neutrophils and eosinophils. As shown in Table 1, the PKC inhibitor staurosporine (0.1–1.0 μM) significantly inhibited the increases in lipid body numbers induced by arachidonic acid and oleic acid. In addition, the selective PKC inhibitor chelerythrine (0.5–1.0 μM) also inhibited arachidonic acid- and oleic acid-induced lipid body formation by 90% and 71%, respectively, at the highest concentrations used, thus further implicating PKC activation in lipid body formation. To determine if cis-unsaturated fatty acid-stimulated induction of neutrophil lipid bodies was also mediated by phospholipase C (PLC) activation, two specific PLC inhibitors were used, U-73122 and D(609), a phosphatidylcholine-specific PLC inhibitor. As shown in Table 1, arachidonic acid-induced lipid body formation was significantly inhibited by 84% and 85% when neutrophils were pretreated with D(609) (1 μM) and U-73122 (5 μM), respectively. Thus, cis-unsaturated fatty acid-induced lipid body formation is mediated by two major intracellular signaling pathways. To further evaluate mechanisms involved in lipid body formation, the dependence of lipid body formation on gene transcription and protein synthesis was investigated. Inhibitors of mRNA and protein synthesis, actinomycin D and cycloheximide, respectively, significantly inhibited both arachidonic acid- and oleic acid-induced lipid body formation as shown in Table 1. These inhibitors were not cytotoxic and did not alter numbers of preformed lipid bodies in neutrophils, suggesting that induction of lipid body formation by cis-unsaturated fatty acids is dependent on specific gene expression and de novo protein synthesis.

tion of $PGE_2$, $LTB_4$ or $LTC_4$ by human neutrophils and eosinophils. To induce lipid body formation, leukocytes were incubated with increasing concentrations of arachidonic acid (3.7–15 $\mu$M) or oleic acid (2.5–10 $\mu$M) for 1 hour. After incubation, lipid bodies were enumerated and replicate leukocytes were stimulated with a sub-maximal dose of calcium ionophore A23187 (0.5 $\mu$M). The results of these experiments are shown in FIGS. 1A, 1B, 2A and 2B. Both arachidonic acid and oleic acid-induced dose-dependent priming for enhanced $LTB_4$, $LTC_4$ and $PGE_2$ production was

TABLE 1

Effect of protein kinase C, phospholipase C, and protein synthesis inhibitors on arachidonate- and oleate-induced lipid body formation in human neutrophils[1]

| Treatment | Dose $\mu$M | Arachidonic Acid lipid bodies (mean ± SEM)/cell | % inhibition | Oleic Acid lipid bodies (mean ± SEM)/cell | % inhibition |
|---|---|---|---|---|---|
| staurosporine | 0 | 7.5 ± 0.3 | — | 9.1 ± 0.3 | — |
|  | 0.1 | 6.1 ± 0.3* | 36% | 8.3 ± 0.3 | 15% |
|  | 1 | 5.1 ± 0.2% | 64% | 7.7 ± 0.3* | 25% |
| chelerythrine | 0 | 8.5 ± 0.3 | — | 8.4 ± 0.3 | — |
|  | 0.5 | 7.5 ± 0.3* | 50% | 7.5 ± 0.2 | 25% |
|  | 1 | 5.1 ± 0.3* | 90% | 5.8 ± 0.3* | 71% |
| D609 | 0 | 8.4 ± 0.3 | — | 10.5 ± 0.4 | — |
|  | 1 | 6.5 ± 0.2* | 48% | 9.4 ± 0.3* | 19% |
|  | 10 | 5.2 ± 0.2* | 84% | 7.8 ± 0.2* | 46% |
| U-73122 | 0 | 8.7 ± 0.3 | — | 20.5 ± 0.5 | — |
|  | 1 | 6.6 ± 0.2* | 45% | 19.3 ± 0.4* | 8% |
|  | 5 | 4.9 ± 0.2* | 85% | 16.9 ± 0.4* | 24% |
| actinomycin D | 0 | 10.6 ± 0.4 | — | 9.9 ± 0.3 | — |
|  | 1 | 8.4 ± 0.3* | 47% | 8.8 ± 0.3 | 26% |
|  | 10 | 7.6 ± 0.3* | 64% | 8.1 ± 0.3* | 42% |
| cycloheximide | 0 | 10.6 ± 0.4 | — | 9.9 ± 0.3 | — |
|  | 1 | 9.8 ± 0.3 | 17% | 9.0 ± 0.3 | 22% |
|  | 10 | 9.2 ± 0.3* | 30% | 8.3 ± 0.3* | 38% |

[1]Neutrophils ($10^6$/ml) were pretreated with protein kinase C (staurosporine, chelerythrine) or protein synthesis inhibitors (actinomycin D, cycloheximide) for 30 min or with phospholipase C inhibitors (D609, U-73122) for 1 h. The cells were then stimulated with vehicle, arachidonic acid (15 $\mu$M), or oleic acid (10 $\mu$M), for 1 h. Results are mean ± SEM from fifty consecutively counted neutrophils. Statistically significant differences between the agonist alone and the inhibitor are represented by an asterisk(*). Percent inhibition has been calculated after subtracting out the basal number of lipid bodies/PMN present prior to stimulation.

Example 2

Involvement of Lipid Bodies in Leukocyte Priming for $PGE_2$, $LTB_4$ and $LTC_4$ Production Materials and Methods Purification of human leukocytes, priming with cis-unsaturated fatty acids and lipid body enumeration were performed as described above.

$PGE_2$, $LTB_4$, and $LTC_4$ Measurement

Human leukocytes ($10^6$ cells/mL) were stimulated with arachidonic acid (3.7, 7.5, 15 $\mu$M), oleic acid (2.5, 5, 10 $\mu$M), or vehicle at 37° C. for 60 min to induce lipid body formation. After the incubation time, a sample was taken for lipid body enumeration and the cells were washed in $Ca^{++}$/$Mg^{++}$ free HBSS. Leukocytes were resuspended in 1 mL of HBSS containing $Ca^{++}$/$Mg^{++}$ and then stimulated with A23187 (0.5 $\mu$M) for 15 min. The reaction was stopped on ice, and the samples were centrifuged at 1500 rpm for 10 min at 4° C. The concentrations of $PGE_2$, $LTB_4$, and $LTC_4$ in the supernatants were assayed by ELISA according to the manufacturer's instructions (Cayman, Ann Arbor, Mich.).

Results

The results of this study established that an increase in number of lipid bodies is associated with increased producconsistently found. Arachidonic acid induced 3.5-, 2.3-, and 1.4-fold increases in the production of $PGE_2$ and $LTB_4$ by neutrophils and $LTC_4$ by eosinophils, respectively, at the highest arachidonic acid concentration (15 $\mu$M). Oleic acid, a cis-unsaturated fatty acid that is not itself an eicosanoid precursor, induced 2.0-, 2.0- and 1.7-fold increases in the production of $PGE_2$, and $LTB_4$ by neutrophils and $LTC_4$ by eosinophils, respectively, at the highest oleic acid concentration (10 $\mu$M). Furthermore, statistically significant positive correlations between the number of lipid bodies in leukocytes formed in response to oleic acid and the priming for enhanced $PGE_2$ (r: 0.99, p<0.01) , $LTB_4$ (r: 0.96, p<0.05) and $LTC_4$ (r: 0.95, p<0.05) release were demonstrable, thus suggesting that lipid bodies may contribute to enhanced eicosanoid formation by leukocytes.

Example 3

Effect of Aspirin and Other NSAIDs on cis-unsaturated Fatty Acid-Induced Lipid Body Formation Methods and Materials Investigations with Mouse Macrophages Cyclooxygenase-1 and cyclooxygenase-2 knockout mice were generated as recently described (Morham et al., *Cell*

83:473–482 (1995); Langenbach et al., *Cell* 83:483–492 (1995)). All experiments were carried out with male 8–12 week old mice. Macrophages from cyclooxygenase genetically deficient mice and wild-type litter mates were obtained by lavaging the peritoneal cavity with 5 mL of cold RPMI containing heparin (20 IU/mL).

Arachidonic Acid Uptake

Neutrophils ($10^6$/mL) were labeled with $^{14}$C-arachidonic acid (0.01 μCi/sample) together with either vehicle, aspirin (10 μg/mL), indomethacin (1 μg/mL) or sodium salicylate (10 μg/mL) for 1 hour. After the incubation period, lipid body formation was elicited by arachidonic acid (15 μM). The cells were washed 3 times in $Ca^{++}$/$Mg^{++}$ free HBSS and analysis of incorporated $^{14}$C-arachidonic acid in the cell pellet was performed by liquid scintillation counting.

Results

Figure 3A:
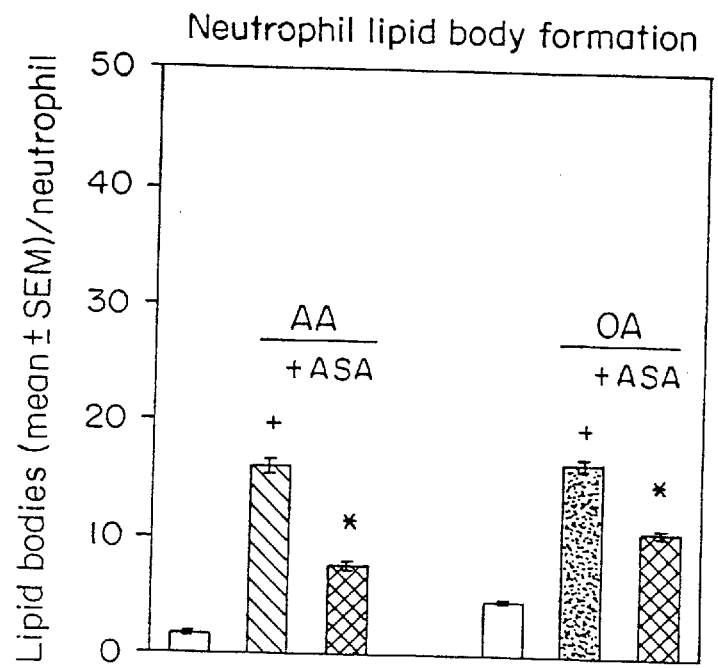
FIG. 3A shows the effect of aspirin (ASA) on arachidonic acid (AA)- and oleic acid (OA)-induced lipid body formation in human neutrophils. Vehicle alone is represented by the dark columns. AA and OA are represented by the striped and gray columns, respectively. Agonist plus the pretreatment with aspirin is represented by the cross-hatched columns. Cells ($10^6$/mL) were pretreated with aspirin (10 $\mu$g/mL) or vehicle for one hour and then stimulated arachidonic acid (15 $\mu$M), oleic acid (10 $\mu$M or vehicle for one hour. Lipid bodies were enumerated by light microscopy following osmium staining. Each point represents the mean±SEM from fifty consecutively counted cells. The statistically significant difference between the vehicle alone and the agonist is represented by a cross. Statistically significant differences due to pretreatment with aspirin are indicated by an asterisk.
Figure 3B:
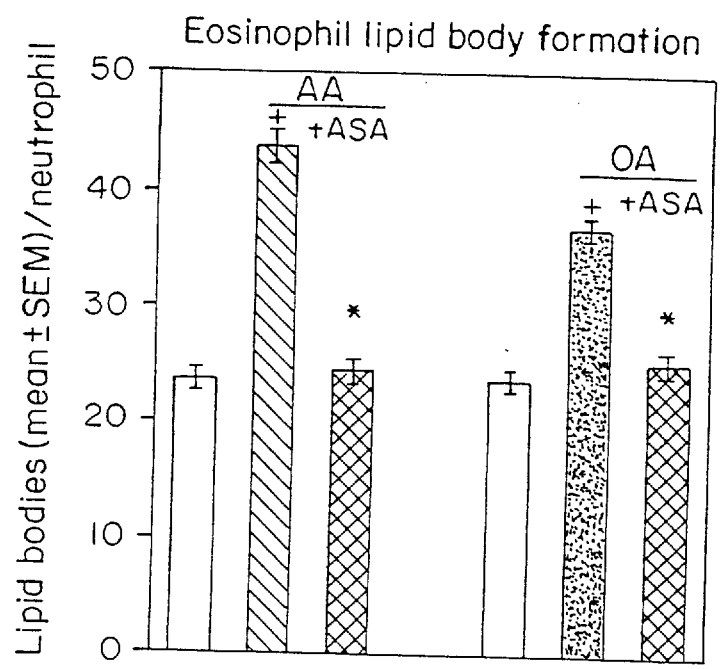
FIG. 3B shows the effect of aspirin (ASA) on arachidonic acid (AA)- and oleic acid (OA)-induced lipid body formation in human eosinophils. Vehicle alone is represented by the dark columns. AA and OA are represented by the striped and gray columns, respectively. Agonist plus the pretreatment with aspirin is represented by the cross-hatched columns. Cells ($10^6$/mL) were pretreated with aspirin (10 $\mu$g/mL) or vehicle for one hour and then stimulated arachidonic acid (15 $\mu$M), oleic acid (10 $\mu$M) or vehicle for one hour. Lipid bodies were enumerated by light microscopy following osmium staining. Each point represents the mean±SEM from fifty consecutively counted cells. The statistically significant difference between the vehicle alone and the agonist is represented by a cross. Statistically significant differences due to pretreatment with aspirin are indicated by an asterisk.

The results of this study established that aspirin, indomethacin, piroxicam and sodium salicylate each inhibit cis-unsaturated fatty acid-induced lipid body formation in neutrophils and eosinophils and that this activity is independent of cyclooxygenase. Aspirin (10 μg/mL) significantly inhibited lipid body formation induced by either arachidonic acid or oleic acid in both neutrophils and eosinophils as shown in FIGS. 3A and 3B. The effect of other NSAIDs on lipid body formation was also investigated. As shown in Table 2, two other cyclooxygenase inhibitors, indomethacin and piroxicam, and a non-inhibitor of cyclooxygenase, sodium salicylate, also significantly inhibited increases in lipid body numbers elicited by arachidonic acid and oleic acid in human neutrophils. The mechanism by which aspirin and these other NSAIDs inhibit lipid body formation was first evaluated by testing whether these compounds acted by blocking fatty acid uptake by cells. The data in Table 3 show that the effects of NSAIDs on lipid body formation were not attributable to inhibition of fatty acid uptake, since aspirin (10 μg/mL), sodium salicylate (10 μg/mL) and indomethacin (1 μg/mL) failed to inhibit $^{14}$C-arachidonic acid uptake in arachidonic acid-stimulated cells.

TABLE 3

Effect of cyclooxygenase inhibitors on $^{14}$C-arachidonic acid uptake[1]

| Treatment | Stimuli | $^{14}$C-AA (cpm) |
|---|---|---|
| vehicle | vehicle | 3200 |
| vehicle | arachidonate | 8121 |
| aspirin | arachidonate | 6974 |
| Na salicylate | arachidonate | 7292 |
| indomethacin | arachidonate | 7095 |

[1]The cells were pretreated with $^{14}$C-arachidonic acid (0.01 μCi/sample) plus vehicle, aspirin (10 μg/ml), sodium salicylate (10 μg/ml) or indomethacin (1 μg/ml) 1 h before the incubation with arachidonic acid (15 μM). Cells were washed 3 times before the analysis of incorporated $^{14}$C-arachidonic acid. Results are representative of 3 independent experiments.

Figure 4:
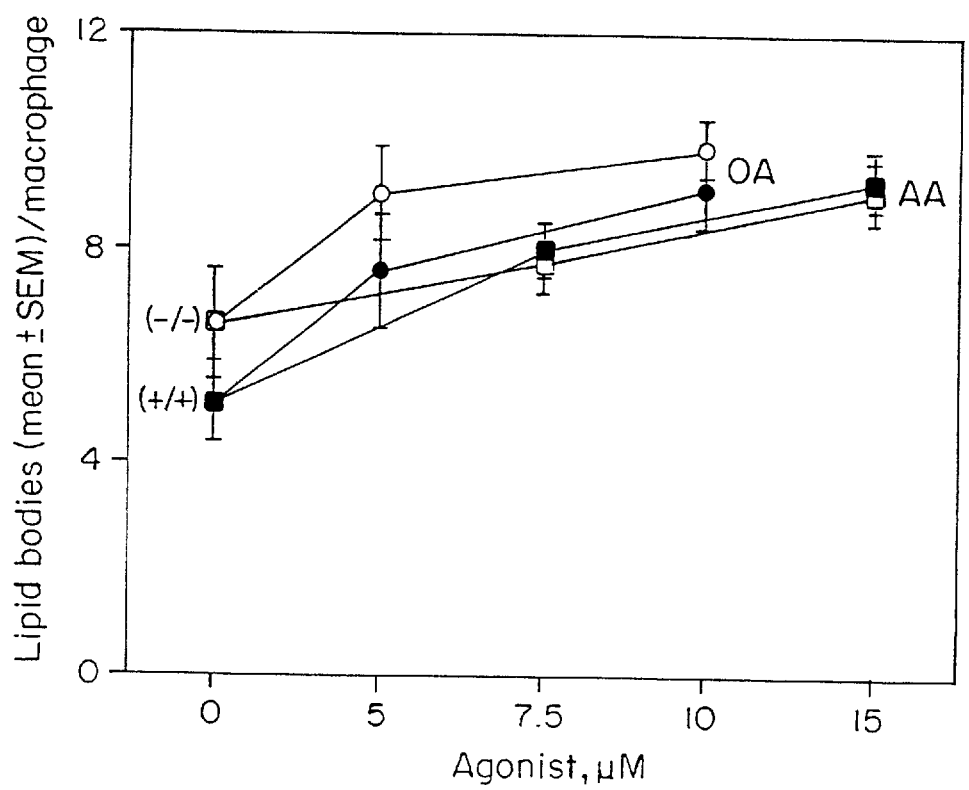
FIG. 4 is a graph illustrating the effects of arachidonic acid and oleic acid on lipid body formation in peritoneal macrophages from wild type (+/+) and cyclooxygenase-1 knockout (−/−) mice. The agonists AA and OA are represented by the square and circle symbols, respectively. The closed symbols represent the wild type mice; the open symbols represent the cyclooxygenase-1 knockout mice. Macrophages ($10^6$/mL) were incubated with the agonists AA and OA at varying concentrations for an hour. Lipid bodies were enumerated using light microscopy following osmium staining. Each point represents the mean±SEM from fifty consecutively scanned macrophages.

To investigate if the inhibitory effect of NSAIDs on cis-unsaturated fatty acid-induced lipid body formation depends upon cyclooxygenase-1 or cyclooxygenase-2 inhibition, leukocytes from wild-type and cyclooxygenase-1 and cyclooxygenase-2 knockout mice were studied. As in human cells, wild-type mouse macrophages and neutrophils contain only a few lipid bodies under normal conditions and can also be stimulated in vitro to produce lipid bodies with arachidonic acid (3.7–15 μM) or oleic acid (2.5–10 μM). Interestingly, arachidonic acid and oleic acid, in all the concentrations analyzed, induced lipid body formation in macrophages from cyclooxygenase-1 and cyclooxygenase-2 deficient mice and no differences in lipid body induction by cis-unsaturated fatty acids were noted between wild-type and cyclooxygenase knockout cells. These data are illustrated in FIG. 4. Furthermore, sodium salicylate (10 μg/mL) and indomethacin (10 μg/mL) significantly inhibited lipid body formation in macrophages from both wild-type and cyclooxygenase-1-deficient mice as indicated in Table 4.

TABLE 2

Effect of NSAIDs on arachidonate- and oleate-induced lipid body formation in human neutrophils[1]

| Treatment | Dose | Arachidonic Acid (15 μM) | | Oleic Acid (10 μM) | |
|---|---|---|---|---|---|
| | | lipid bodies (mean ± SEM) PMN | % inhibition | lipid bodies (mean ± SEM) PMN | % inhibition |
| vehicle | — | 16.0 ± 0.6 | — | 16.3 ± 0.6 | — |
| indomethacin | 1 μg/ml | 7.0 ± 0.5* | 63% | 9.1 ± 0.5* | 61% |
| Na salicylate | 10 μg/ml | 7.9 ± 0.4* | 56% | 10.1 ± 0.4* | 53% |
| piroxicam | 10 μg/ml | 7.2 ± 0.4* | 61% | 10.4 ± 0.4* | 50% |

[1]Neutrophils ($10^6$/ml) were pretreated with the NSAID or vehicle for 1 h then stimulated with vehicle, arachidonic acid, or oleic acid for 1 h. Values of lipid body numbers in resting neutrophils were 1.6 ± 0.2 and 4.5 ± 0.3 for AA and OA, respectively. Results are mean ± SEM from fifty consecutively counted neutrophils. Statistically significant differences between the agonist alone and the NSAID are represented by an asterisk (*). Percent inhibition has been calculated after subtracting out the basal number of lipid bodies/PMN present prior to stimulation.

TABLE 4

Effect of NSAIDs on peritoneal macrophages from wild type and COX 1 knockout mice[1]

| Treatment | Dose | Stimuli | wild type lipid bodies (mean ± SEM)/ macrophage | % inhibition | COX 1 knockout lipid bodies (mean ± SEM)/ macrophage | % inhibition |
|---|---|---|---|---|---|---|
| — | — | vehicle | 2.9 ± 0.2 | — | 2.5 ± 0.2 | — |
| — | — | AA | 6.8 ± 0.3+ | — | 7.0 ± 0.5+ | — |
| indomethacin | 1 µg/ml | AA | 4.4 ± 0.3* | 61% | 4.8 ± 0.4* | 48% |
| Na salicylate | 10 µg/ml | AA | 5.0 ± 0.3* | 45% | 4.0 ± 0.4* | 66% |

[1]Peritoneal macrophages from wild type and COX 1 knockout mice were pretreated with the NSAID or vehicle for 1h and then stimulated with arachidonic acid (AA, 15 µM) or vehicle for 1h. Results are mean ± SEM from fifty consecutively counted macrophages. The statistically significant difference between AA and the vehicle is marked by a cross (+). Statistically significant differences between the AA and pretreatment with the NSAID is marked by an asterisk(*).

Figure 5A:
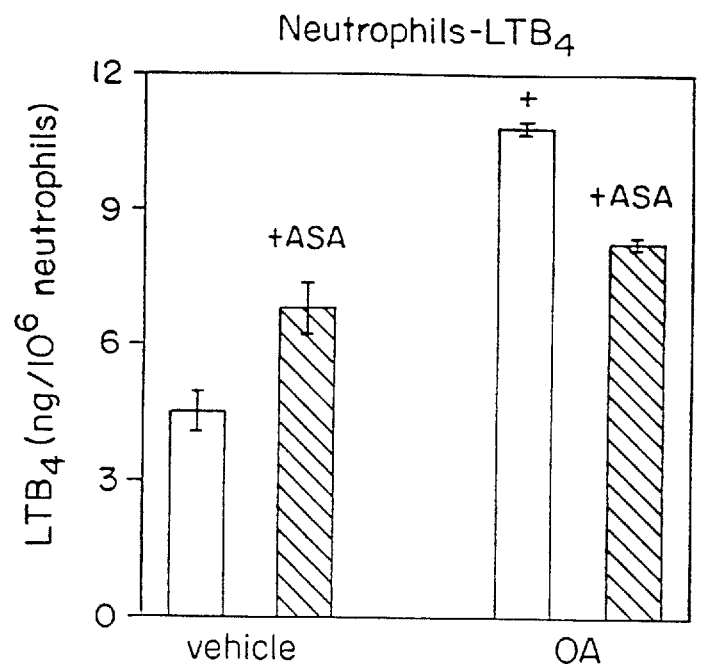
FIG. 5A is a graph showing that aspirin inhibits cis-unsaturated fatty acid-induced priming for enhanced leukotriene $B_4$ ($LTB_4$) production in human neutrophils. Striped and open columns represent vehicle treated cells and aspirin treated cells, respectively. Cells ($10^6$/mL) were pretreated with aspirin (10 $\mu$g/mL) or vehicle for one hour and then stimulated with OA (10 $\mu$M) or vehicle for one hour. The concentration of $LTB_4$ in the supernatant was measured by ELISA after incubation with A23187 (0.5 $\mu$M) for 15 minutes at 37° C. Data are expressed as mean from 2–4 independent assays performed in duplicate. The statistically significant difference between the vehicle alone and the agonist is represented by a cross. Statistically significant differences due to pretreatment with aspirin are indicated by an asterisk.
Figure 5B:
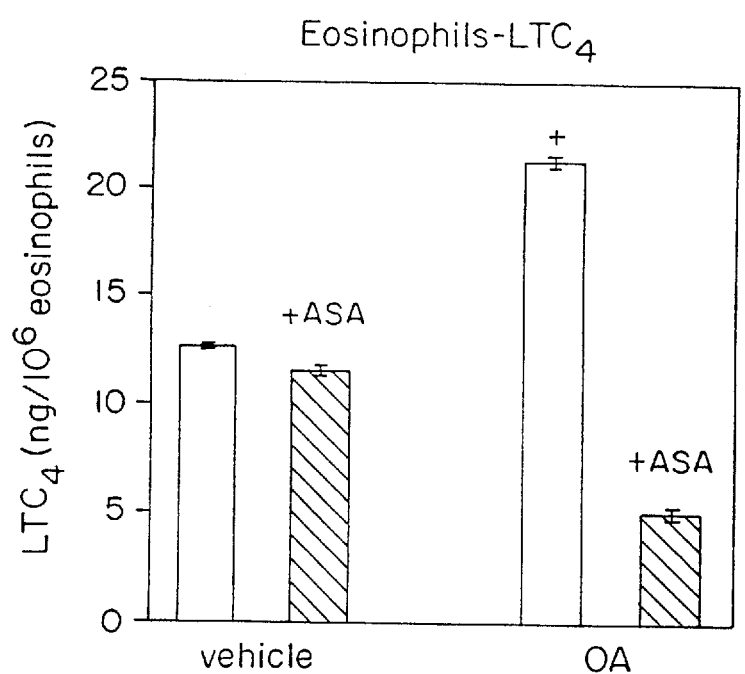
FIG. 5B is a graph showing that aspirin inhibits cis-unsaturated fatty acid-induced priming for enhanced leukotriene $C_4$ ($LTC_4$) production in human eosinophils. Striped and open columns represent vehicle treated cells and aspirin treated cells, respectively. Cells ($10^6$/mL) were pretreated with aspirin (10 $\mu$g/mL) or vehicle for one hour and then stimulated with OA (10 $\mu$M) or vehicle for one hour. The concentration of $LTC_4$ in the supernatant was measured by ELISA after incubation with A23187 (0.5 $\mu$M) for 15 minutes at 37° C. Data are expressed as mean from 2–4 independent assays performed in duplicate. The statistically significant difference between the vehicle alone and the agonist is represented by a cross. Statistically significant differences due to pretreatment with aspirin are indicated by an asterisk.

Because aspirin was effective in blocking lipid body formation induced by cis-unsaturated fatty acids and lipid body numbers correlated with enhanced eicosanoid formation, the ability of aspirin to inhibit both cyclooxygenase and lipoxygenase pathway-derived eicosanoid production was investigated. Pretreatment of leukocytes with aspirin (10 µg/mL) inhibited $PGE_2$ production by neutrophils and eosinophils, but this could be due solely to inhibition of cyclooxygenase. In contrast, aspirin does not directly affect lipoxygenase pathways. Aspirin, however, significantly inhibited oleic acid-induced priming for enhanced $LTB_4$ production by neutrophils and $LTC_4$ production by eosinophils, as shown in FIGS. 5A and 5B. A similar inhibitory effect of aspirin was also observed for arachidonic acid-induced priming for leukotriene production. Aspirin was not acting to block pathways of arachidonate release or metabolism that are activated by calcium ionophore, since it failed to inhibit calcium ionophore-induced $LTB_4$ and $LTC_4$ production in cells not pre-stimulated with cis-unsaturated fatty acids.

EQUIVALENTS

Those skilled in the art will recognize or be able to ascertain using no more than routine experimentation many equivalents to the specific embodiments of the invention described herein. Such equivalents are intended to be encompassed in the scope of the following claims.

We claim:

1. A method for assessing the ability of a compound to inhibit inflammation, comprising the steps of:
    (a) contacting a plurality of cells with a compound to be assessed;
    (b) priming the cells of (a) for lipid body formation;
    (c) determining the extent of lipid body formation in the cells;
    (d) comparing the extent of lipid body formation in the cells with the extent of lipid body formation in control cells,
wherein if the extent of lipid body formation determined in (c) is less than the extent of lipid body formation in control cells, the compound is an inhibitor of lipid body formation; and, if the compound is an inhibitor of lipid body formation,
    (e) assessing the inflammatory activity of the compound in an animal model of inflammation or in a human.

2. The method of claim 1 wherein step (b) precedes step (a).

3. The method of claim 1 wherein step (a) and step (b) are conducted simultaneously.

4. The method of claim 1 wherein the extent of lipid body formation is determined by enumeration of lipid bodies.

5. The method of claim 1 wherein the cells are derived from a vertebrate.

6. The method of claim 5 wherein the vertebrate is selected from the group consisting of human, mouse, rat, guinea pig, dog, cat, horse and pig.

7. The method of claim 5 wherein the cells derived from a vertebrate are leukocytes, muscle cells, fibroblasts, endothelial cells, mesenchymal cells, epithelial cells, platelets or tumor cells.

8. The method of claim 7 wherein the leukocytes are neutrophils, eosinophils, lymphocytes, macrophages or monocytes.

9. The method of claim 1 wherein the cells are primed for lipid body formation by contacting the cells with an agent which induces lipid body formation.

10. The method of claim 9 wherein the agent which induces lipid body formation is a protein kinase C activator.

11. The method of claim 9 wherein the agent which induces lipid body formation is a cis-unsaturated fatty acid.

12. The method of claim 11 wherein the cis-unsaturated fatty acid is arachidonic acid or oleic acid.

13. The method of claim 10 wherein the protein kinase C activator is a phorbol ester or a diglyceride.

14. The method of claim 13 wherein the phorbol ester is phorbol-12-myristate-13-acetate or phorbol-12,13-dibutyrate.

15. The method of claim 13 wherein the diglyceride is 1-oleyl-2-acetyl-glycerol.

16. The method of claim 9 wherein the agent which induces lipid body formation is elicited by PAF stimulation or is a product of a lipoxygenase-catalyzed process.

17. The method of claim 1 wherein the lipid bodies are stained prior to determining the extent of lipid body formation.

18. The method of claim 17 wherein the lipid bodies are stained with an osmium compound or a lipophilic stain.

19. The method of claim 18 wherein the osmium compound is osmium tetroxide.

20. The method of claim 17 wherein the lipid bodies are stained by incorporation of fluorescent lipids.

21. The method of claim 4 wherein the lipid bodies are enumerated using light or electron microscopy.

22. A method for assessing the ability of a compound to inhibit inflammation, comprising the steps of:
    (a) combining a plurality of cells primed for lipid body formation with a compound to be assessed;

(b) determining the extent of lipid body formation in the cells; and (c) comparing the extent of lipid body formation in (b) with the extent of lipid body formation in control cells, wherein if the extent of lipid body formation determined in (b) is less than the extent of lipid body formation in control cells, the compound is an inhibitor of lipid body formation; and, if the compound is an inhibitor of lipid body formation, (d) assessing the inflammatory activity of the compound in an animal model of inflammation or in a human.

* * * * *